United States Patent
Liu et al.

(10) Patent No.: US 11,395,928 B2
(45) Date of Patent: Jul. 26, 2022

(54) SYSTEMS AND METHODS FOR CT IMAGING IN IMAGE-GUIDED RADIOTHERAPY

(71) Applicant: SHANGHAI UNITED IMAGING HEALTHCARE CO., LTD., Shanghai (CN)

(72) Inventors: Jian Liu, Shanghai (CN); Yuelin Shao, Shanghai (CN); Xiao Fang, Shanghai (CN); Cheng Ni, Shanghai (CN)

(73) Assignee: SHANGHAI UNITED IMAGING HEALTHCARE CO. LTD., Shanghai (CN)

( * ) Notice: Subject to any disclaimer, the term of this patent is extended or adjusted under 35 U.S.C. 154(b) by 265 days.

(21) Appl. No.: 16/236,415

(22) Filed: Dec. 29, 2018

(65) Prior Publication Data

US 2019/0209869 A1  Jul. 11, 2019

Related U.S. Application Data

(63) Continuation of application No. PCT/CN2018/072270, filed on Jan. 11, 2018.

(51) Int. Cl.
*A61N 5/10* (2006.01)
*A61B 6/03* (2006.01)
*A61B 6/00* (2006.01)

(52) U.S. Cl.
CPC ......... *A61N 5/1067* (2013.01); *A61N 5/1071* (2013.01); *A61N 5/1081* (2013.01);
(Continued)

(58) Field of Classification Search
CPC .. A61N 5/1067; A61N 5/1081; A61N 5/1071; A61N 2005/1061; A61B 6/032; A61B 6/4283; A61B 6/5264
See application file for complete search history.

(56) References Cited

U.S. PATENT DOCUMENTS

| 7,085,347 B2 * | 8/2006 | Mihara ................. A61N 5/10 378/197 |
| 2006/0113482 A1 * | 6/2006 | Pelizzari ............. A61N 5/1065 250/370.09 |

(Continued)

FOREIGN PATENT DOCUMENTS

| CN | 102908159 A | 2/2013 |
| CN | 103071241 A | 5/2013 |
| CN | 104971442 A | 10/2015 |

OTHER PUBLICATIONS

International Search Report in PCT/CN2018/072270 dated Sep. 28, 2018, 4 pages.

(Continued)

*Primary Examiner* — Marcus H Taningco
(74) *Attorney, Agent, or Firm* — Metis IP LLC

(57) ABSTRACT

A system and method for image-guided radiotherapy are provided. The system may include a treatment assembly and an imaging assembly. The treatment assembly may include a first radiation source configured to deliver a treatment beam. The treatment assembly may have a treatment region relating to an object. The imaging assembly may include a second radiation source and a radiation detector. The second radiation source may be configured to deliver an imaging beam, and the radiation detector may be configured to detect at least a portion of the imaging beam. The imaging assembly may have an imaging region relating to the object. The first radiation source may be rotatable in a first plane, and the second radiation source may be rotatable in a second plane different from the first plane, such that the treatment region and the imaging region at least partially overlap.

19 Claims, 10 Drawing Sheets

(52) U.S. Cl.
CPC ............. *A61B 6/032* (2013.01); *A61B 6/4283* (2013.01); *A61N 2005/1061* (2013.01)

(56) References Cited

U.S. PATENT DOCUMENTS

| | | | |
|---|---|---|---|
| 2009/0180589 A1* | 7/2009 | Wang | A61N 5/1082 |
| | | | 378/65 |
| 2012/0035470 A1* | 2/2012 | Kuduvalli | A61N 5/10 |
| | | | 600/427 |
| 2013/0101082 A1 | 4/2013 | Jordan et al. | |
| 2016/0325119 A1* | 11/2016 | Yu | A61N 5/1047 |
| 2017/0106208 A1 | 4/2017 | Gauthier et al. | |
| 2018/0304098 A1* | 10/2018 | Humber | A61B 6/4085 |

OTHER PUBLICATIONS

Written Opinion in PCT/CN2018/072270 dated Sep. 28, 2018, 4 pages.

* cited by examiner

SYSTEMS AND METHODS FOR CT IMAGING IN IMAGE-GUIDED RADIOTHERAPY

CROSS-REFERENCE TO RELATED APPLICATIONS

This application is a Continuation of International Application No. PCT/CN2018/072270, filed on Jan. 11, 2018, the contents of which is incorporated herein by reference.

TECHNICAL FIELD

The present disclosure generally relates to systems and methods for image-guided radiotherapy, and more specifically, relates to systems and methods for computed tomography (CT) imaging in image-guided radiotherapy.

BACKGROUND

Image-guided radiotherapy (IGRT) is a tumor treatment technique in which three-dimensional (3D) or two-dimensional (2D) volumetric imaging (or 2D/3D imaging with time) can be used to localize a target tumor and/or tumor motion. In some IGRT applications, an object (e.g., a patient) subjected to the IGRT may need to be moved between the imaging (e.g., computed tomography [CT] imaging) position and the treatment position. The imaging operation and treatment operation may be complicated and prone to error due to, e.g., table sagging, real time change or motion of internal organs including and in the vicinity of a treatment target, or the like, or a combination thereof. Thus, it is desirable to provide systems and methods for imaging of an object at the treatment position during a treatment process.

SUMMARY

In a first aspect of the present disclosure, a system for image-guided radiotherapy may include a treatment assembly and an imaging assembly. The treatment assembly may include a first radiation source configured to deliver a treatment beam. The treatment assembly may have a treatment region relating to an object. The imaging assembly may include a second radiation source and a radiation detector. The second radiation source may be configured to deliver an imaging beam, and the radiation detector may be configured to detect at least a portion of the imaging beam. The imaging assembly may have an imaging region relating to the object. The first radiation source may be rotatable in a first plane, and the second radiation source may be rotatable in a second plane different from the first plane, such that the treatment region and the imaging region at least partially overlap.

In some embodiments, the treatment beam may pass through an isocenter of the imaging assembly.

In some embodiments, the treatment beam and the imaging beam may intersect at the isocenter of the imaging assembly.

In some embodiments, the system may further include a first gantry supporting the first radiation source, and a second gantry supporting the second radiation source and the radiation detector.

In some embodiments, the first radiation source may be located outside of a bore defined by the first gantry.

In some embodiments, the system may further include an arm mounted on the first gantry, the first radiation source being mounted on the arm.

In some embodiments, the first radiation source may be located within a bore defined by the first gantry.

In some embodiments, the first radiation source may be mounted on an inner side of the first gantry.

In some embodiments, a rotation plane of the first gantry and a rotation plane of the second gantry may be parallel.

In some embodiments, a rotation plane of the second gantry may be tilted with respect to a rotation plane of the first gantry.

In some embodiments, the first gantry and the second gantry may be rotatable.

In some embodiments, the first gantry and the second gantry may rotate synchronously.

In some embodiments, the first gantry may be configured to rotate independently of the second gantry.

In some embodiments, the system may further include a processing module configured to reconstruct an image based on the at least portion of the imaging beam detected by the radiation detector.

In some embodiments, the processing module may reconstruct the image when the first radiation source delivers the treatment beam.

In some embodiments, the processing module, based on the reconstructed image, may cause the first radiation source to deliver an adjusted treatment beam.

In some embodiments, the processing module, based on the reconstructed image, may cause a position of the object to be adjusted with respect to the treatment beam.

In some embodiments, the delivery of the treatment beam and the delivery of the imaging beam may be simultaneous or alternate.

In some embodiments, the radiation detector may be a flat panel detector or a computed tomography detector.

In some embodiments, the second plane may be parallel to the first plane.

In some embodiments, the second plane may be tiled by an angle with respect to the first plane.

In some embodiments, the angle may be an acute angle.

In some embodiments, the acute angle may range between 0° and 45°.

In a second aspect of the present disclosure, a system for image-guided radiotherapy may include a treatment assembly and an imaging assembly. The treatment assembly may include a first radiation source configured to deliver a treatment beam. The imaging assembly may include a second radiation source and a radiation detector. The second radiation source may be configured to deliver an imaging beam, and the radiation detector may be configured to detect at least a portion of the imaging beam. The imaging beam may form an imaging beam rotation plane during rotation of the imaging assembly. The treatment beam may intersect with the imaging beam rotation plane.

In a third aspect of the present disclosure, a system for image-guided radiotherapy may include a treatment assembly and an imaging assembly. The treatment assembly may include a first radiation source configured to deliver a treatment beam. The treatment beam may form a treatment beam rotation surface during rotation of the first radiation source. The imaging assembly may include a second radiation source and a radiation detector. The second radiation source may be configured to deliver an imaging beam, and the radiation detector may be configured to detect at least a portion of the imaging beam. The imaging beam may intersect with the treatment beam rotation surface.

In a fourth aspect of the present disclosure, a system for image-guided radiotherapy may include a treatment assembly and an imaging assembly. The treatment assembly may include a first radiation source configured to deliver a treatment beam. The treatment beam may form a treatment beam rotation surface during rotation of the first radiation source. The imaging assembly may include a second radiation source and a radiation detector. The second radiation source may be configured to deliver an imaging beam, and the radiation detector may be configured to detect at least a portion of the imaging beam. The imaging beam may form an imaging beam rotation plane during rotation of the imaging assembly. The imaging beam rotation plane may intersect with the treatment beam rotation surface such that a portion of a subject is irradiated by the imaging beam and the treatment beam.

In a fifth aspect of the present disclosure, a method for image-guided radiotherapy may include one or more of the following operations. A first image of an object may be obtained. A region of interest in the first image may be determined. The object may be positioned in a radiotherapy system including a treatment assembly and an imaging assembly. An imaging beam may be delivered, by the imaging assembly, to the object. At least a portion of the imaging beam may be detected, by the imaging assembly, to generate an imaging dataset.

A second image including the region of interest may be generated based on the imaging dataset. The treatment beam may be delivered, by the treatment assembly and based on the second image, toward a target portion of the object. The target portion of the object may correspond to the region of interest. The treatment beam and the imaging beam may be substantially in different planes.

In some embodiments, the delivering a treatment beam and the delivering an imaging beam may be simultaneous or alternate.

In some embodiments, the delivering the treatment beam toward the target portion may include one or more of the following operations. A movement or change of the target portion may be detected based on the second image. The delivery of the treatment beam may be revised based on the detected movement or change of the target portion.

In some embodiments, the revising the delivery of the treatment beam may include at least one of pausing the delivery, resuming the delivery, or terminating the delivery.

In some embodiments, a notification may be further generated based on the detected movement or change of the region of interest.

In some embodiments, the treatment beam may intersect with an imaging beam rotation plane defined by the imaging beam.

In some embodiments, the treatment beam may pass through an isocenter of the imaging assembly.

In some embodiments, the treatment beam and the imaging beam may intersect at the isocenter of the imaging assembly.

In a sixth aspect of the present disclosure, a system for image-guided radiotherapy may include a treatment assembly and an imaging assembly. The treatment assembly may include a first radiation source configured to deliver a treatment beam. The imaging assembly may include a second radiation source and a radiation detector. The second radiation source may be configured to deliver an imaging beam, and the radiation detector may be configured to detect at least a portion of the imaging beam. The first radiation source may be configured to rotate about a rotation axis of the treatment assembly, defining a plane. The treatment beam may be tilted with respect to the plane such that the treatment beam passes an imaging region of the imaging assembly. In some embodiments, the treatment beam may pass an isocenter of the imaging assembly. The isocenter of the imaging assembly may be located within the imaging region. Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
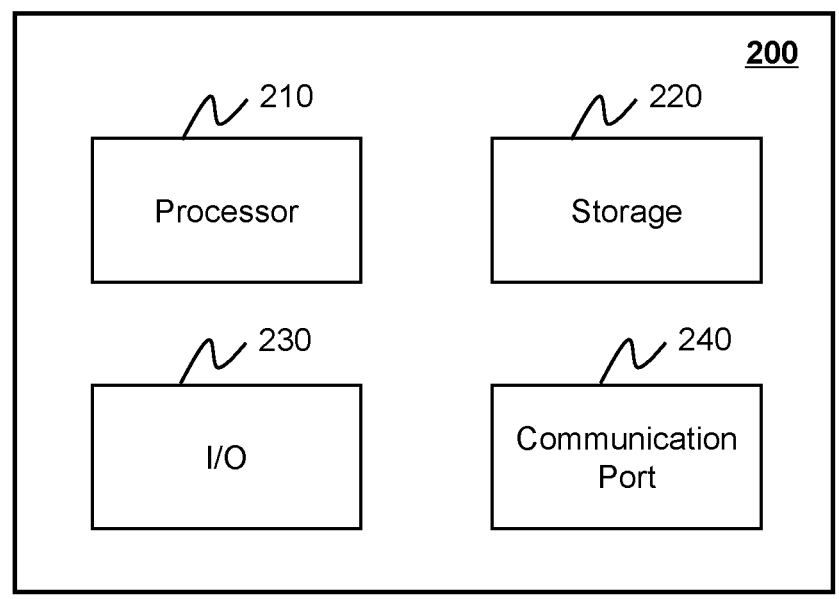
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for imaging an object during radiotherapy. With the image-guided radiotherapy device disclosed in the present disclosure, the object may not need to be moved between the imaging position and the treatment position.

Figure 1:
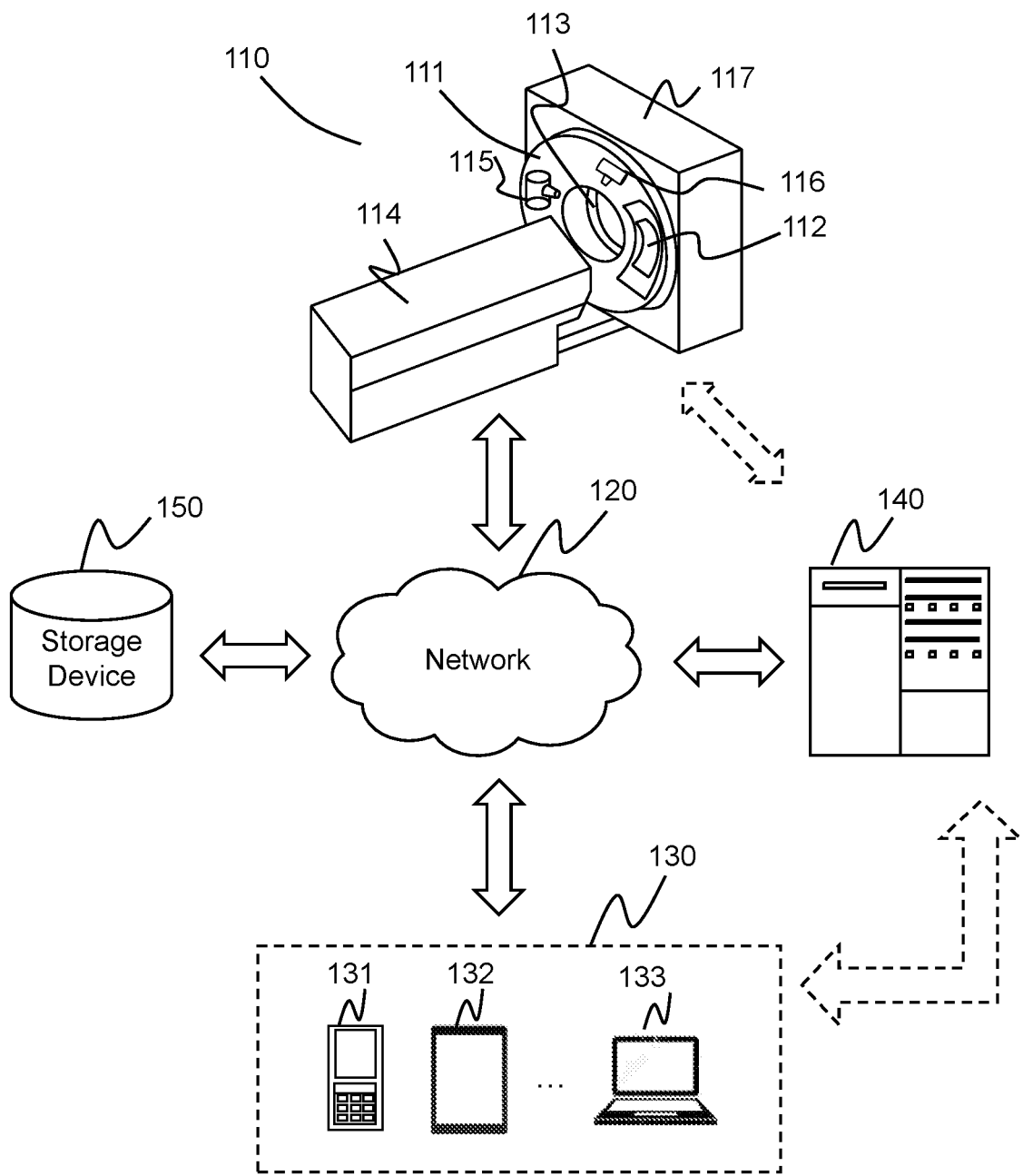
FIG. 1 is a schematic diagram illustrating an exemplary radiation system according to some embodiments of the present disclosure.

FIG. 1 is a schematic diagram illustrating an exemplary radiation system 100 according to some embodiments of the present disclosure. The radiation system 100 may include an image-guided treatment apparatus 110, a network 120, one or more terminals 130, a processing device 140, and a storage device 150.

The image-guided treatment apparatus 110 may deliver radiation toward an object (e.g., a patient or a portion thereof) based on an image of the object. A source of the radiation may emit one or more radiation rays including, for example, X-rays, α-rays, β-rays, γ-rays, etc. In some embodiments, the image of the object may be generated by an imaging device such as a computed tomography (CT) device, a magnetic resonance imaging (MRI) device, a positron emission tomography (PET) device, a single photon emission computed tomography (SPECT) device, or the like, or any combination thereof. For illustration purposes, the following descriptions are provided with reference to a CT device as the imaging device or assembly. It is understood that it is not intended to limit the scope of the present disclosure. Other imaging devices may be incorporated into the image-guided treatment apparatus 110.

The image of the object may be used to determine and/or track the location of a target region of the object. In some embodiments, the target region may be a portion of the object, for example, a head, a breast, a lung, an abdomen, a large intestine, a small intestine, a bladder, a gallbladder, a pancreas, a prostate, a uterus, an ovary, a liver, or the like, or a portion thereof, or any combination thereof. In the present disclosure, "object" and "subject" are used interchangeably. In some embodiments, the target region may include an abnormal tissue, for example, a tumor, a polyp, etc. In some embodiments, the radiation rays may be delivered toward the target region for radiotherapy based on the determined or tracked location of the target region. In some embodiments, the radiation rays for radiotherapy may be also referred to as treatment beams.

In some embodiments, the image-guided treatment apparatus 110 may include a treatment assembly (e.g., a treatment radiation source 116, a gantry 111, an accelerator not shown in FIG. 1), an imaging assembly (e.g., one or more radiation ray emitters 115, one or more radiation ray detectors 112, etc.), and an auxiliary assembly (e.g., a table 114, a base 117). The base 117 may be configured to support the gantry 111. The gantry 111 may be configured to support the treatment radiation source 116, the accelerator, the radiation ray emitters 115, the radiation ray detectors 112, etc. An object may be placed on the table 114 for treatment and/or imaging. In some embodiments, the gantry 111 may define a bore 113 to accommodate at least a portion of the table 114 and/or the object. More descriptions of the image-guided treatment apparatus 110 may be found elsewhere in the present disclosure (e.g., FIG. 4 and the description thereof).

The network 120 may include any suitable network that can facilitate the exchange of information and/or data for the radiation system 100. In some embodiments, one or more components of the radiation system 100 (e.g., the image-guided treatment apparatus 110, the terminal(s) 130, the processing device 140, or the storage device 150) may communicate information and/or data with one or more other components of the radiation system 100 via the network 120. For example, the processing device 140 may obtain data corresponding to radiation signals from the image-guided treatment apparatus 110 via the network 120. As another example, the processing device 140 may obtain user instructions from the terminal(s) 130 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation system 100 may be connected to the network 120 to exchange data and/or information.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 130 may remotely operate the image-guided treatment apparatus 110. In some embodiments, the terminal(s) 130 may operate the image-guided treatment apparatus 110 via a wireless connection. In some embodiments, the terminal(s) 130 may receive information and/or instructions inputted by a user, and send the received information and/or instructions to the image-guided treatment apparatus 110 or to the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted.

The processing device 140 may process data and/or information obtained from the image-guided treatment apparatus 110, the terminal(s) 130, and/or the storage device 150. For example, the processing device 140 may process data corresponding to radiation signals of one or more detectors obtained from the image-guided treatment apparatus 110 and reconstruct an image of the object. In some embodiments, the reconstructed image may be transmitted to the terminal(s) 130 and displayed on one or more display devices in the terminal(s) 130. In some embodiments, the processing device 140 may be a single server, or a server group. The server group may be centralized, or distributed. In some embodiments, the processing device 140 may be local or remote. For example, the processing device 140 may access information and/or data stored in the image-guided treatment apparatus 110, the terminal(s) 130, and/or the storage device 150 via the network 120. As another example, the processing device 140 may be directly connected to the image-guided treatment apparatus 110, the terminal(s) 130, and/or the storage device 150 to access stored information and/or data. As a further example, the processing device 140 may be integrated in the image-guided treatment apparatus 110. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation system 100 (e.g., the processing device 140, the terminal(s) 130, etc.). One or more components of the radiation system 100 may access the data or instructions stored in the storage device 150 via the network 120. In some embodiments, the storage device 150 may be directly connected to or communicate with one or more components of the radiation system 100 (e.g., the processing device 140, the terminal(s) 130, etc.). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data obtained from the image-guided treatment apparatus 110, the terminal(s) 130, the storage device 150, and/or any other component of the radiation system 100. Specifically, the processor 210 may process one or more measured data sets obtained from the image-guided treatment apparatus 110. For example, the processor 210 may perform one-dimensional (1D) correction or two-dimensional (2D) correction for the measured data set(s). The processor 210 may reconstruct an image based on the corrected data set(s). In some embodiments, the reconstructed image may be stored in the storage device 150, the storage 220, etc. In some embodiments, the reconstructed image may be displayed on a display device by the I/O 230. In some embodiments, the processor 210 may perform instructions obtained from the terminal(s) 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the image-guided treatment apparatus 110, the terminal 130, the storage device 150, or any other component of the radiation system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for reducing or removing one or more artifacts in an image.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the image-guided treatment apparatus 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
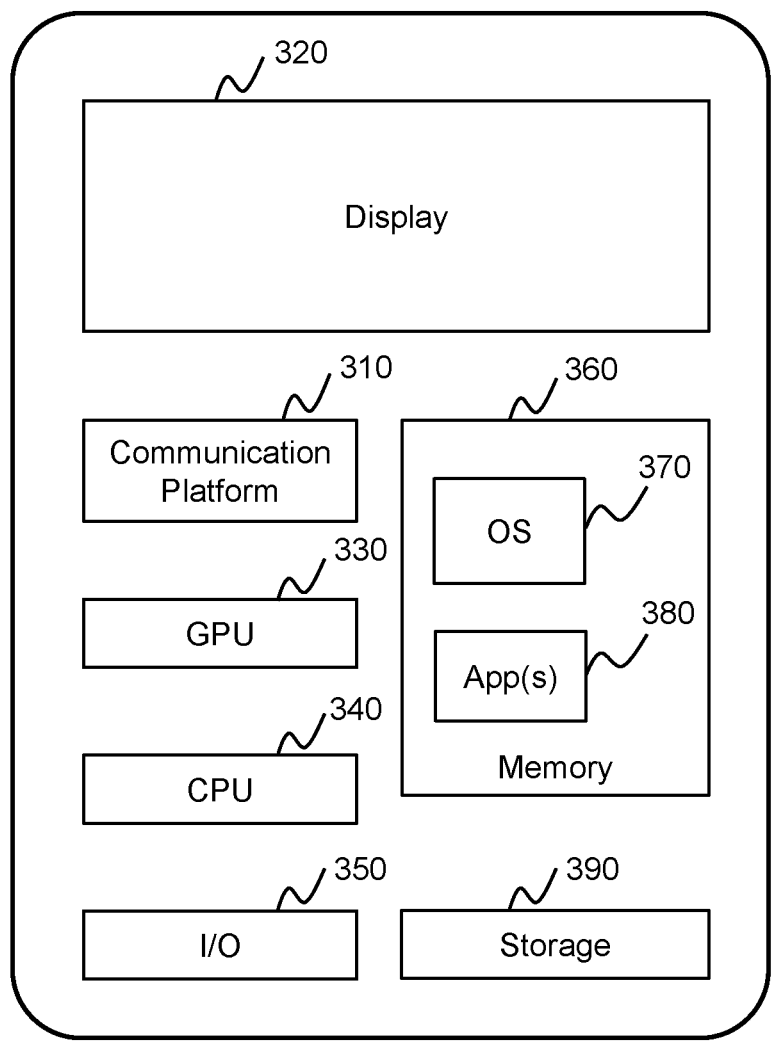
FIG. 3 is a schematic diagram illustrating exemplary hardware and/or software components of an exemplary mobile device on which the terminal may be implemented according to some embodiments of the present disclosure.

FIG. 3 is a schematic diagram illustrating exemplary hardware and/or software components of an exemplary mobile device 300 according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image with reduced Nyquist ghost artifact as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 4:
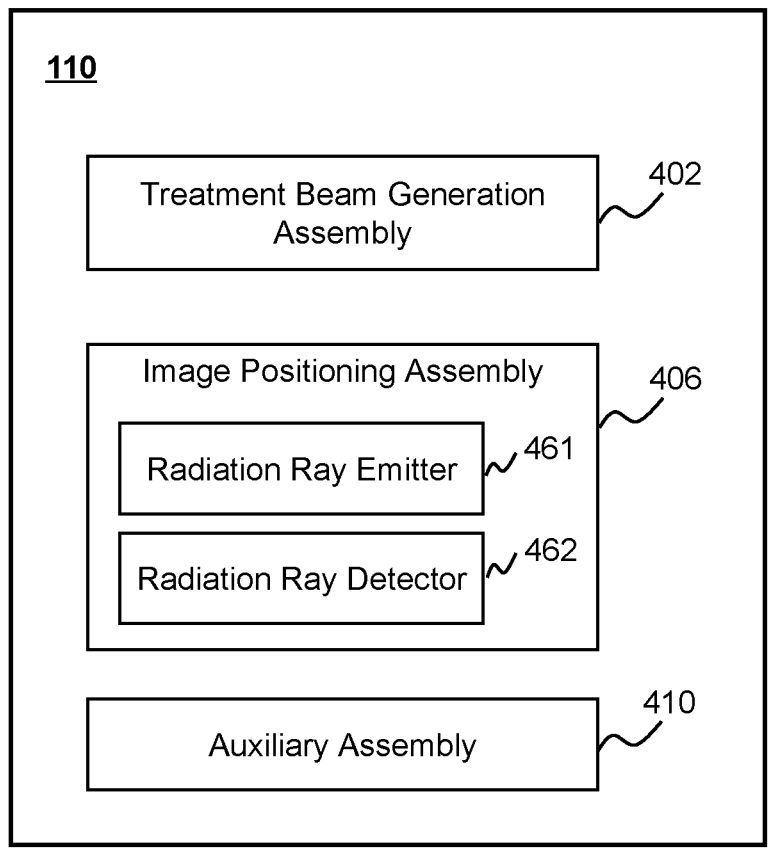
FIG. 4 is a block diagram illustrating an exemplary image-guided treatment device according to some embodiments of the present disclosure.

FIG. 4 is a block diagram illustrating an exemplary image-guided treatment apparatus 110 according to some embodiments of the present disclosure. The image-guided treatment apparatus 110 may include a treatment beam generation assembly 402, an imaging assembly 406 and an auxiliary assembly 410.

The treatment beam generation assembly 402 may be configured to deliver a treatment beam toward a target portion of an object (e.g., a patient). In some embodiments, the target portion may need to be subjected to radiotherapy. In some embodiments, the radiotherapy may be delivered in the form of a treatment beam. In some embodiments, the target portion may be a cell mass, a tissue, an organ (e.g., a prostate, a lung, a brain, a spine, a liver, a pancreas, a breast, etc.), or any combination thereof. In some embodiments, the target portion may be a tumor, an organ with a tumor, or a tissue with a tumor. The treatment beam may include a particle beam, a photon beam, or the like, or any combination thereof. The particle beam may include a stream of neutrons, protons, electrons, heavy ions, or the like, or any combination thereof. The photon beam may include an X-ray beam, a γ-ray beam, an α-ray beam, a β-ray beam, an ultraviolet beam, an ultrasound beam (e.g., a high intensity focused ultrasound beam), a laser beam, or the like, or any combination thereof. The shape of the X-ray beam may be a line, a narrow pencil, a narrow fan, a fan, a cone, a wedge, or the like, or any combination thereof. The energy level of the treatment beam may be suitable for radiotherapy. For example, an X-ray beam delivered by the treatment beam generation assembly 402 may have an energy of megavoltage (MV) level. Merely by way of example, the energy of the X-ray beam may be 6 MV. It should be noted that in some embodiments, one or more thermal techniques may be used to treat the target portion, and the treatment may also be image-guided.

The treatment beam generation assembly 402 may deliver the treatment beam to the target portion based on a real-time location of the target portion despite that the target portion is in motion. In some embodiments, the treatment beam generation assembly 402 may determine the delivery of the treatment beam to the target portion according to a predetermined treatment plan. The predetermined treatment plan may include a radiation dose, a radiation rate (the amount of radiation delivered per unit time), a radiation time, or the like, or any combination thereof. For example, the treatment beam generation assembly 402 may start the delivery of the treatment beam to the target portion when the location of the target portion is conformed to the predetermined treatment plan. In some embodiments, the treatment beam generation assembly 402 may determine the delivery of the treatment beam to the target portion according to a real-time location of the target portion. During the treatment, the motion of the target portion may be tracked and the real-time location of the target portion may be determined by the imaging assembly 406.

In some embodiments, the treatment beam generation assembly 402 may have a treatment region. As used herein, the treatment region may refer to a region that may be irradiated by the treatment beam emitted by the treatment beam generation assembly 402. In some embodiments, the target portion of the object may be positioned in the treatment region for treatment.

In some embodiments, the treatment beam generation assembly 402 may include a first radiation source, and/or a radiation source support. The first radiation source may be configured to deliver the treatment beam to the target portion. In some embodiments, the first radiation source may include a linear accelerator (linac) configured to generate the treatment beam. The radiation source support may be configured to support the first radiation source. In some embodiments, the first radiation source may be mounted on the radiation source support. In some embodiments, the first radiation source may be rotatable through its mounting on the radiation source support. In some embodiments, the radiation source support may include a first gantry and/or an arm one end of which is attached to the first gantry, and the first radiation source may be rotatable through its mounting on the first gantry and/or the arm. For example, the radiation source support may include a rotatable first gantry made of steel, or any other suitable material. The first radiation source may be mounted on (e.g., fixedly mounted on) the first gantry. As another example, the radiation source support may include a rotatable first gantry and an arm. The arm may be mounted on (e.g., fixedly mounted on) the first gantry via one end thereof or form an integral part of the first gantry (e.g., an integral part of the cover of the first gantry), and the first radiation source may be mounted on (fixedly mounted on) the arm.

In some embodiments, the treatment beam generation assembly 402 (e.g., the first radiation source and/or the support assembly on which it is mounted) may rotate about the rotation axis of the treatment beam generation assembly 402. The rotation of the treatment beam generation assembly 402 (e.g., a certain point of the treatment beam generation assembly 402) about the rotation axis of the treatment beam generation assembly 402 may define a rotation plane of the treatment beam generation assembly 402 (or referred to as a first axial rotation plane). When the treatment beam generation assembly 402 rotates about the rotation axis of the treatment beam generation assembly 402, a center ray of the treatment beam of the treatment beam generation assembly 402 may rotate about the rotation axis accordingly. The rotation of the center ray of the treatment beam of the treatment beam generation assembly 402 may form a plane that may be called a treatment beam rotation surface (or referred to as a first beam rotation surface). In some embodiments, as illustrated in FIG. 6B and FIG. 7B, the treatment beam rotation surface may be a three-dimensional surface (e.g., a conical surface). As used herein, the center ray of the treatment beam may refer to the ray that passes through the center (e.g., the focus) of the first radiation source. In some embodiments, the center ray of the treatment beam may pass the isocenter of the imaging assembly 406.

The imaging assembly 406 may be configured to perform imaging to, e.g., generate an image of the target portion, determine a real-time location of the target portion, and/or track the motion of the target portion during a radiotherapy operation performed by the treatment beam generation assembly 402. In some embodiments, the location of the target portion of the object may change with time due to various motions, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, or the like, or any combination thereof. The location of the target portion may be monitored based on an image (e.g., a CT image, a CBCT image, an MRI image, a PET image, a PET-CT image, etc.) of the object acquired by the imaging assembly 406 before, during, and/or after the radiotherapy operation.

In some embodiments, the imaging assembly 406 may have an imaging region. As used herein, the imaging region of the imaging assembly 406 may refer to a region that may be irradiated by imaging beam(s) emitted by the imaging assembly 406. The imaging region of the imaging assembly 406 may include an isocenter of the imaging assembly. As used herein, the isocenter of the imaging assembly 406 may be defined as the axis of rotation of the imaging assembly 406, at the point where it intersects the plane of rotation.

In some embodiments, the imaging assembly 406 may include at least one radiation source 461 and at least one radiation detector 462. The radiation source 461 (or referred to as a second radiation source) may be configured to deliver an imaging beam to the object. The imaging beam may include a particle beam, a photon beam, or the like, or any combination thereof. The particle beam may include a stream of neutrons, protons, electrons, heavy ions, or the like, or any combination thereof. The photon beam may include an X-ray beam, a γ-ray beam, an α-ray beam, a β-ray beam, an ultraviolet beam, a laser beam, or the like, or any combination thereof. The shape of the X-ray beam may be a line, a narrow pencil, a narrow fan, a fan, a cone, a wedge, a tetrahedron, or the like, or any combination thereof. For example, the radiation source may be a CBCT radiation source and the imaging beam may be a cone beam. The energy level of the imaging beam may be suitable for imaging. In some embodiments, the energy level of the imaging beam may be different from that of the treatment beam generated by the treatment beam generation assembly 402. For example, an X-ray beam delivered by the radiation source 461 may have an energy of a kilovoltage (kV) level. Merely by way of example, the energy of the X-ray beam may be 90 kVp. In some embodiments, X-rays delivered by two or more radiation sources 461 may have different energy levels.

The radiation detector 462 may be configured to detect at least a portion of the imaging beam emitted from the radiation source 461 to generate imaging data (e.g., projection data). The imaging data may be transmitted to the processing device 140 for further processing. The processing device 140 may reconstruct an image of the object or a portion thereof based on the imaging data. The location of the target portion of the object may be determined based on the image.

In some embodiments, the radiation detector 462 may include one or more detector units. A detector unit may include a scintillator detector (e.g., a cesium iodide detector, a gadolinium oxysulfide detector), a gas detector, etc. In some embodiments, the detector units may be arranged in a single row, two rows, or any other number of rows. Merely by way of example, the radiation detector 462 may be a CT detector configured to detect X-rays. The shape of the radiation detector 462 may be flat, arc-shaped, circular, or the like, or any combination thereof. For example, the radiation detector 462 may be a flat panel detector. In some embodiments, the radiation source 461 may deliver dual energy X-rays, and accordingly, the imaging data generated by the radiation detector 462 may be amenable to processing with one or more operations suitable for tomosynthesis imaging. In some embodiments, a dual layer detector, or photon counting detector, may be employed to obtain energy information from the impinging X-ray beam.

In some embodiments, the imaging assembly 406 may include a support assembly. The support assembly may be configured to support the radiation source 461 and/or the radiation detector 462. In some embodiments, the support assembly may include a second gantry. In some embodiments, the radiation source 461 (and/or the radiation detector 462) may be mounted on the support assembly, and the radiation source 461 (and/or the radiation detector 462) may be rotatable through its mounting on the support assembly. For example, the support assembly may include a rotatable second gantry, and the radiation source 461 (and/or the radiation detector 462) may be mounted on (e.g., fixedly mounted on) the second gantry.

In some embodiments, the imaging assembly 406 (e.g., the radiation source 461 and/or the radiation detector 462, or the support assembly on which they are mounted) may rotate about the rotation axis of the imaging assembly 406 or the isocenter of the imaging assembly 406. The rotation of the imaging assembly 406 (e.g., a certain point of the imaging assembly 406) about the rotation axis may define a rotation plane of the imaging assembly 406 (or referred to as a second axial rotation plane). During the rotation of the imaging assembly 406 around the rotation axis, the center ray of the imaging beam of the imaging assembly 406 may rotate about the rotation axis accordingly. The rotation of the center ray of the imaging beam around the rotation axis may form an imaging beam rotation plane (or referred to as a second beam rotation plane). As used herein, the center ray of the imaging beam may refer to the ray that passes through the center of the radiation source 461. In some embodiments, the center ray of the imaging beam may pass through the center of the radiation detector 462.

As illustrated, the first gantry of the treatment beam generation assembly 402 and the second gantry of the imaging assembly 406 may be rotatable. In some embodiments, the rotation of the first gantry may be independent of the rotation of the second gantry. For example, the first gantry and the second gantry may rotate driven by independent driving forces, e.g., from two different motors. In some embodiments, the first gantry and the second gantry may rotate synchronously. For example, the rotation of the first gantry and the second gantry may be synchronized mechanically or electronically. In some embodiments, the first gantry may rotate at a same rotation speed as the second gantry. Merely by way of example, at least a portion of the first gantry may be connected to (e.g., fixed to) at least a portion of the second gantry, resulting that the first gantry and the second gantry rotate synchronously, at a same speed. In some embodiments, the connection between the first gantry and the second gantry may be realized by way of overlapping, mortise, occlusion, engagement, or the like. In some embodiments, the first gantry may rotate at a different rotation speed than the second gantry. For instance, the first gantry may rotate at a lower rotation speed than the second gantry. In some embodiments, the different rotation speed may be realized by driving the rotation of the first gantry and the rotation of the second gantry by independent driving forces, e.g., from two different motors. In some embodiments, the different rotation speed may be realized by driving the rotation of the first gantry and the rotation of the second gantry using one motor and a gear box. The gear box may be configured to provide one or more ratios of rotation speeds between the first gantry and the second gantry. For instance, the ratio of the rotation speed of the first gantry to the rotation speed of the second gantry may be 1:1: 1:1.5, 1:2, 1:2.5, etc.

In some embodiments, the first gantry of the treatment beam generation assembly 402 and the second gantry of the imaging assembly 406 may be parallel or non-parallel to each other. The first gantry and/or the second gantry may be rotatable. The first gantry and/or the second gantry may have a corresponding rotation axis (or rotation plane). As used herein, the first gantry may be said to be parallel to the second gantry when the rotation axis (or rotation plane) of the first gantry is parallel to that of the second assembly, and vice versa. In some embodiments, when the first gantry and the second gantry are parallel to each other, the first gantry and the second gantry may share a same rotation axis (or rotation plane). In some embodiments, when the first gantry and the second gantry are parallel to each other, a rotation plane of the treatment beam generation assembly 402 and a rotation plane of the imaging assembly 406 may be co-planar or be in different planes that are parallel to each other. In some embodiments, the treatment beam generation assembly 402 and the imaging assembly 406 may be positioned such that the second beam rotation plane intersects with the first beam rotation surface such that the treatment region and the imaging region at least partially overlap. See, e.g., FIGS. 6A and 6B and the description thereof.

The spatial arrangement of the first gantry and the second gantry may be various. In some embodiments, the first gantry and the second gantry may be placed side by side. In some embodiments, the first gantry and the second gantry at least partially overlap. In some embodiments, the diameter of the second gantry may be smaller than the diameter of the first gantry, and at least part of the second gantry may be located within the bore of the first gantry. See, FIGS. 6 and 7 and the description thereof. In some embodiments, a portion of the first gantry and/or a portion of the second gantry may be connected to avoid a displacement there between that may occur during the treatment or imaging process. In some embodiments, the connection between the first gantry and/or the second gantry may be realized by way of overlapping, mortise, occlusion, engagement, or the like.

In some embodiments, the bore of the first gantry (or referred to as a first bore) and the bore of the second gantry (or referred to as a second bore) may at least partially overlap. The bore(s) may be configured to receive an object to be subjected to radiation in the radiation system 100. In some embodiments, the two bores may share a concentric axis.

In some embodiments, the treatment beam generation assembly 402 (e.g., the first radiation source) and the imaging assembly 406 (e.g., the radiation source 461 and/or the radiation detector 462) may be configured such that the second axial rotation plane is tilted by an angle with respect to the first axial rotation plane. Merely by way of example, the angle may be an acute angle that ranges between 0° and 45°. In some embodiments, the treatment beam generation assembly 402 and the imaging assembly 406 may be positioned such that the treatment region and the imaging region at least partially overlap. In some embodiments, the imaging beam may intersect with the first beam rotation surface. In some embodiments, the treatment beam may intersect with the second beam rotation plane. In some embodiments, the treatment beam generation assembly 402 and the imaging assembly 406 may be positioned such that the treatment region and the imaging region at least partially overlap. See, e.g., FIGS. 7A and 7B and the description thereof.

In some embodiments, the treatment beam generation assembly 402 and the imaging assembly 406 may be positioned such that the treatment beam emitted by the treatment beam generation assembly 402 passes the imaging region of the imaging assembly 406. In some embodiments, the treatment beam generation assembly 402 and the imaging assembly 406 may be positioned such that the treatment beam is tilted with respect to the first axial rotation plane and passes an isocenter of the imaging assembly 406. Detailed description of the treatment beam generation assembly 402 and the imaging assembly 406 may be found elsewhere in the present disclosure. See, e.g., FIGS. 6 and 7 and the descriptions thereof.

The auxiliary assembly 410 may be configured to facilitate operations of the treatment beam generation assembly 402 and/or the imaging assembly 406. In some embodiments, the auxiliary assembly 410 may include a cooling assembly (not shown), a table 114 (as shown in FIG. 1), a base 117 (as shown in FIG. 1), etc. The cooling assembly may be configured to produce, transfer, deliver, channel, or circulate a cooling medium to the image-guided treatment apparatus 110 to absorb heat produced by the image-guided treatment apparatus 110 (e.g., the radiation detector 462) during an imaging procedure and/or radiotherapy operation. The table 114 may be configured to support and/or transport the object (e.g., a patient) to be imaged and/or undergo radiotherapy. The base 117 may be configured to support the treatment beam generation assembly 402 and/or the imaging assembly 406. For example, the base 117 may support one or more gantries on which the treatment beam generation assembly 402 and/or the imaging assembly 406 may be mounted.

It should be noted that the above description of the image-guided treatment apparatus 110 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the image-guided treatment apparatus 110 may include one or more storage devices. As another example, the image-guided treatment apparatus 110 may include a single gantry configured to support the treatment beam generation assembly 402 and the imaging assembly 406. As another example, the image-guided treatment apparatus 110 may further include a detection assembly configured to detect and/or receive signals (e.g., X-ray treatment beams) emitted from the treatment beam generation assembly 402 (e.g., the first radiation source of the treatment beam generation assembly 402).

Figure 5:
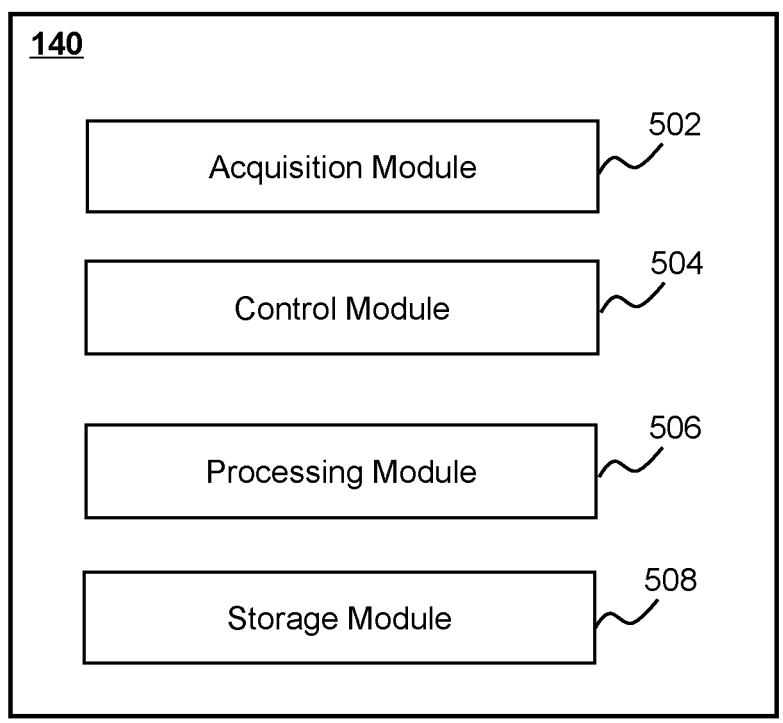
FIG. 5 is a block diagram illustrating an exemplary processing device according to some embodiments of the present disclosure.

FIG. 5 is a block diagram illustrating an exemplary processing device 140 according to some embodiments of the present disclosure. The processing device 140 may include an acquisition module 502, a control module 504, a processing module 506, and a storage module 508. At least a portion of the processing device 140 may be implemented on a computing device as illustrated in FIG. 2 or a mobile device as illustrated in FIG. 3.

The acquisition module 502 may acquire imaging data. In some embodiments, the acquisition module 502 may acquire the imaging data (e.g., CT imaging data) from the image-guided treatment apparatus 110, the terminal 130, the storage device 150, and/or an external data source (not shown). In some embodiments, the imaging data may include raw data (e.g., projection data). For example, the imaging data (e.g., projection data) may be generated based on detected imaging beams at least some of which have passed through an object being imaged and treated in the image-guided treatment apparatus 110. In some embodiments, the acquisition module 502 may acquire one or more instructions for processing the imaging data. The instructions may be executed by the processor(s) of the processing device 140 to perform exemplary methods described in this disclosure. In some embodiments, the acquired imaging data may be transmitted to the storage module 508 to be stored.

The control module 504 may control operations of the acquisition module 502, the storage module 508, the processing module 506 (e.g., by generating one or more control parameters), the image-guided treatment apparatus 110, or the like, or any combination thereof. For example, the control module 504 may cause the acquisition module 502 to acquire imaging data, the timing of the acquisition of the imaging data, etc. As another example, the control module 504 may cause the processing module 506 to process imaging data acquired by the acquisition module 502. In some embodiments, the control module 504 may control the operation of the image-guided treatment apparatus 110. For example, the control module 504 may cause the image-guided treatment apparatus 110 (e.g., the treatment beam generation assembly 402) to start, pause, stop, and/or resume the delivery of the imaging beam and/or the treatment beam to the object. As another example, the control module 504 may cause the image-guided treatment apparatus 110 to adjust the radiation dose of the imaging beam or treatment beam to the object.

The processing module 506 may process information provided by various modules of the processing device 140. The processing module 506 may process imaging data acquired by the acquisition module 502, imaging data retrieved from the storage module 508 and/or the storage device 150, etc. In some embodiments, the processing module 506 may reconstruct one or more images based on the imaging data according to a reconstruction technique. The reconstruction technique may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the processing module 506 may perform pre-processing on the imaging data before the reconstruction. The pre-processing may include, for example, imaging data normalization, imaging data smoothing, imaging data suppressing, imaging data encoding (or decoding), denoising, etc.

In some embodiments, the processing module 506 may analyze one or more images to determine and/or identify a region of interest (ROI) relating to the object based on an image segmentation algorithm. In some embodiments, the processing module 506 may assess and/or monitor the change of the identified ROI relating to the object. The image segmentation algorithm may include a threshold algorithm, a region growing algorithm, an algorithm based on an energy function, a level set algorithm, a region segmentation and/or merging, an edge tracking segmentation algorithm, a statistical pattern recognition algorithm, a mean clustering segmentation algorithm, a model algorithm, a segmentation algorithm based on a deformable model, an artificial neural networks algorithm, a minimum path segmentation algorithm, a tracking algorithm, a segmentation algorithm based on a rule, a coupling surface segmentation algorithm, or the like, or any combination thereof. In some embodiments, the processing module 506 may reconstruct one or more images based on one or more imaging datasets generated at different times in a radiotherapy operation. In some embodiments, based on one or more reconstructed images of an object including a target portion, the processing module 506 may determine a movement or change of the target portion.

In some embodiments, the processing module 506 may determine, based on the images and the analysis thereof, whether any change or adjustment is needed with respect to the treatment plan, and/or determine the needed adjustment. Based on the determined adjustment, the control module 504 may cause the adjustment to be implemented. For instance, the control module 504 may cause the image-guided treatment apparatus 110 to deliver an adjusted treatment beam or cause a position of the object to be adjusted. For example, the processing module 506 may transmit the motion information of the target portion to the control module 504. The control module 504 may accordingly control the image-guided treatment apparatus 110 to adjust the delivery of the treatment beam by for example, pausing the delivery and/or changing the position of the source of the treatment beam. As another example, the control module 504 may accordingly control the image-guided treatment apparatus 110 to adjust the position of the object with respect to the treatment beam.

In some embodiments, the delivery of a treatment plan may be monitored and/or adjusted real time. For instance, based on the imaging data the imaging assembly 406 and/or the acquisition module 502 acquires (e.g., real time), the processing module 506 may automatically generate and/or analyze images to monitor the location of the target portion of the object, and/or assess the change of the location of the target portion, on the basis of which the processing module 506 may determine how to proceed further with the treatment plan (e.g., to continue the radiotherapy as planned, to continue the radiotherapy with a revised plan, or to terminate the radiotherapy, etc.). The processing module 506 may determine the location of the target portion based on the generated image(s). In some embodiments, the monitoring, assessment, and/or adjustment may be performed semi-automatically with the input of a user. For instance, based on the imaging data the imaging assembly 406 and/or the acquisition module 502 acquires (e.g., real time), the processing module 506 may generate one or more images and send them to be presented on a terminal 130 (e.g., a display) so that the user may analyze the images and provide an instruction as to how to proceed further with the treatment plan (e.g., to continue the radiotherapy as planned, to continue the radiotherapy with a revised plan, or to terminate the radiotherapy, etc.). As another example, based on the imaging data the imaging assembly 406 and/or the acquisition module 502 acquires (e.g., real time), the processing module 506 may generate one or more images. The processing module 506 may first analyze the images and determine if any change occurs in the target region and how much the change is. The processing module 506 may determine accordingly if any adjustment in the treatment plan is needed. If the change of the target region or the adjustment needed in the treatment plan is within a threshold, the processing module 506 may determine the adjustment automatically and send it to, e.g., the control module 504, to be implemented. In some embodiments, a notification may be generated when the processing module 506 makes such a determination. If the change of the target region or the adjustment needed in the treatment plan is within a threshold, the processing module 506 may generate a notification to, e.g., the user (e.g., the doctor) to seek instructions from the user as to how to proceed further.

The storage module 508 may store imaging data, control parameters, processed imaging data, or the like, or a combination thereof. In some embodiments, the storage module 508 may store one or more programs and/or instructions that may be executed by the processor(s) of the processing device 140 to perform exemplary methods described in this disclosure. For example, the storage module 508 may store program(s) and/or instruction(s) that can be executed by the processor(s) of the processing device 140 to acquire imaging data of an object, reconstruct one or more images based on the imaging data, determine an ROI in the image(s), detect a movement or change of a target portion of the object based on the image(s), revise the delivery of the treatment beam to the target portion, and/or adjust the position of the object relative to the treatment beam based on the detected movement or change of the target portion.

In some embodiments, one or more modules illustrated in FIG. 5 may be implemented in at least part of the radiation system 100 as illustrated in FIG. 1. For example, the acquisition module 502, the control module 504, the processing module 506, and/or the storage module 508 may be implemented via the processing device 140 and/or the terminal 130. Via the terminal 130, a user may set parameters for scanning a subject, controlling imaging processes, adjusting parameters for reconstructing an image, etc.

Figure 6A:
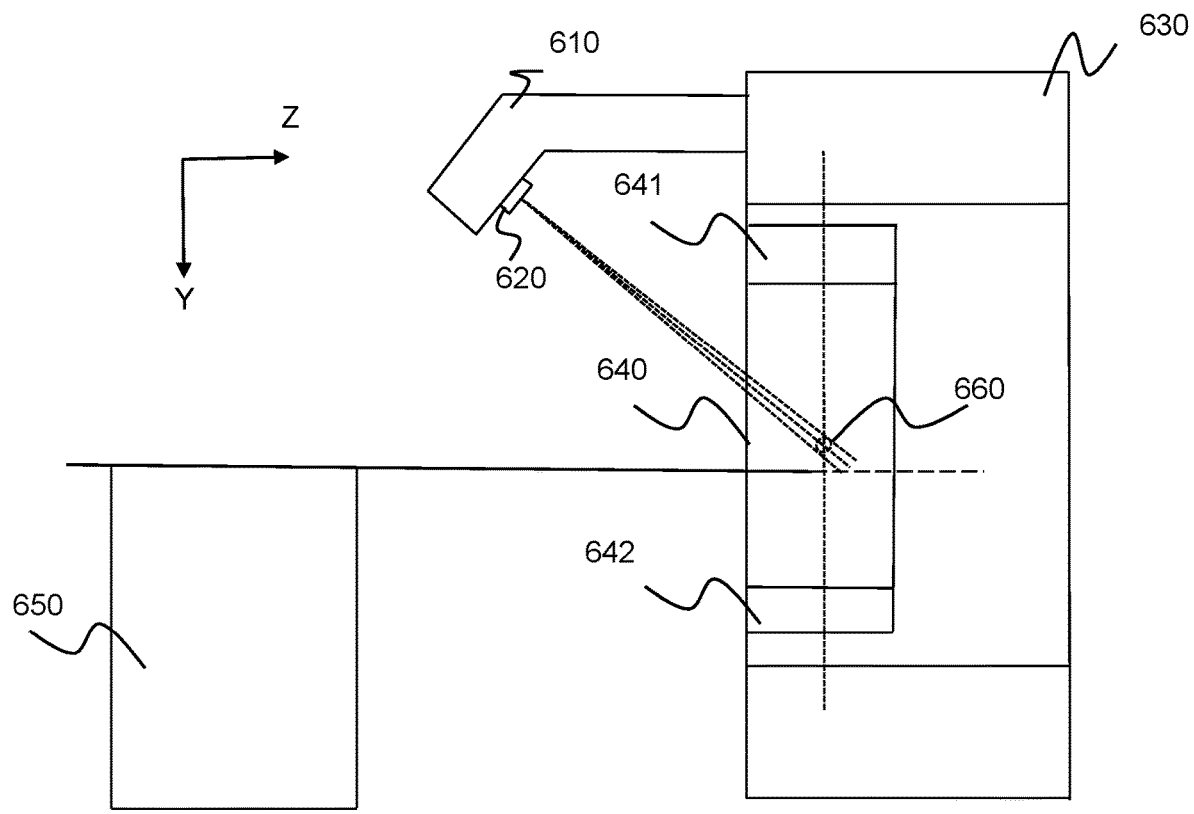
FIG. 6A is a schematic diagram illustrating the section view of an exemplary image-guided treatment device according to some embodiments of the present disclosure.
Figure 6B:
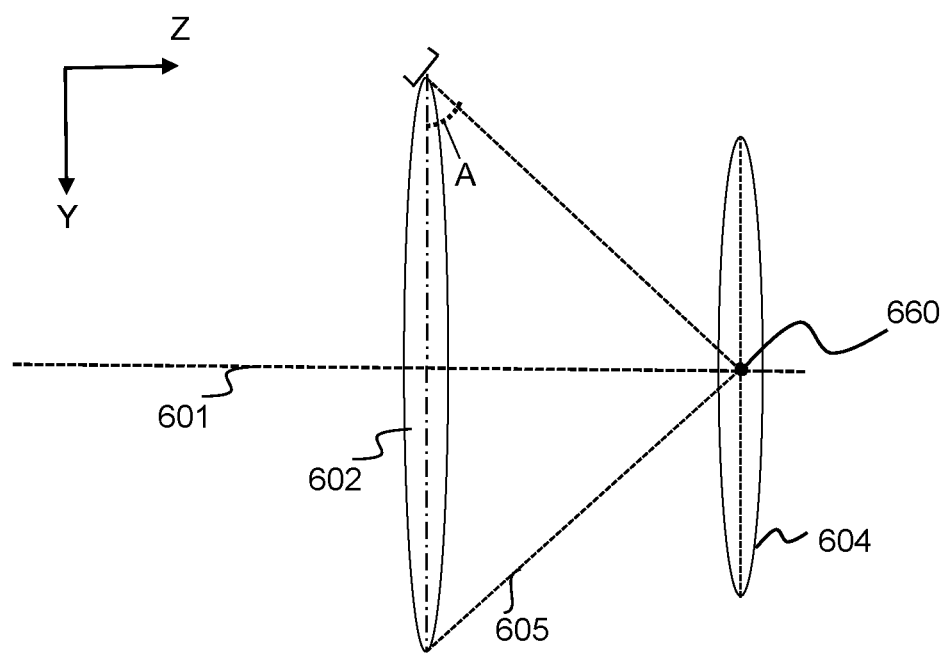
FIG. 6B is a schematic diagram illustrating rotation planes and beam rotation planes according to some embodiments of the present disclosure.

FIG. 6A is a schematic diagram illustrating the section view in a Y-Z plane of an exemplary image-guided treatment apparatus 110 according to some embodiments of the present disclosure. In the present disclosure, the Z axis direction may be from the right side to the left side of the image-guided treatment apparatus 110, as shown in FIGS. 1, 6A, 6B, 7A, and 7B. The Y axis direction may be from the upper part to the lower part of the image-guided treatment apparatus 110, as shown in FIGS. 1, 6A, 6B, 7A, and 7B. The X axis direction may be from the front side to the rear side of the image-guided treatment apparatus 110 along the axis of the bore, as shown in FIG. 1. FIG. 6B is a schematic diagram illustrating rotation planes and beam rotation planes according to some embodiments of the present disclosure.

The image-guided treatment apparatus 110 may include a first gantry 630, a second gantry 640, an arm 610, a first radiation source 620 coupled to one end of the arm 610, a second radiation source 641, a radiation detector 642 opposing the radiation source, a table 650 and a base at least supporting the first gantry 630 (not shown). Both of the first gantry 630 and the second gantry 640 are ring-shaped. The other end of the arm 610 may be mounted on the first gantry 630. The second gantry 640 may support the second radiation source 641 and the radiation detector 642. The second gantry 640 may be directly mounted on the base, or may be supported by the first gantry 630. The second gantry 640 may serve as a stator, and the second radiation source 641 and the radiation detector 642 may serve as a rotor mounted on the second gantry 640 (the stator) in rotation. In some embodiments, the second gantry 640 may serve as a rotor on which the second radiation source 641 and the radiation detector 642 may be fixedly connected. When the second gantry 640 serves as the rotor, the coupling between the second gantry 640 and the base or the connection between the second gantry 640 and the first gantry 630 may be rotatable. The table 650 may be configured to support and/or transport the object (e.g., a patient) to be imaged and/or undergo radiotherapy.

The rotation plane of the first gantry 630 and the rotation plane of the second gantry 640 may be parallel to each other. In some embodiments, as shown in FIG. 6A, the diameter of the second gantry may be smaller than the diameter of the hole defined by the first gantry. At least a portion of the second gantry 640 may be located within the first gantry 630. Specifically, the first gantry 630 may include a first bore. The second gantry 640 may include a second bore. At least a portion of the second gantry may be located within the first bore. In some embodiments, the first bore and the second bore may share a same rotation axis 601 as shown in FIG. 6B. In some embodiments, the first bore and/or the second bore may be configured to receive an object (e.g., a patient) to be subjected to radiation (e.g., radiation of treatment beams, radiation of imaging beams) in the radiation system 100.

In some embodiments, the first gantry and the second gantry may be rotatable. In some embodiments, the rotation of the first gantry may be independent of the rotation of the second gantry. For example, the first gantry may rotate with a rotation speed lower than that of the second gantry. In some embodiments, the first gantry (or the first radiation source 620), and/or the second gantry (or the second radiation source 641, and/or the detector 642) may rotate synchronously. See, e.g., relevant description in FIG. 4.

The first gantry 630 may support the first radiation source 620. For example, as illustrated, the first radiation source 620 may be mounted on an inner side of the first gantry 630. In some other embodiments, the first radiation source 620 may be mounted on a side of the first gantry 630. The first radiation source 620 may be configured to deliver a treatment beam (e.g., X-ray beam) to a target portion of an object. In some embodiments, the treatment beam may cover a treatment region of the radiation system 100. The treatment region may be located in a center region of the first gantry 630. The first radiation source 620 may rotate about the rotation axis 601 of the first gantry 630. The rotation of the first radiation source 620 about the rotation axis 601 of the first gantry 630 may define the first axial rotation plane 602. When the first radiation source 620 rotates about the rotation axis 601, the center ray of the treatment beam may rotate about the rotation axis 601 accordingly, defining a first beam rotation surface 605 (or referred to as the treatment beam rotation surface). As illustrated in FIG. 6A, the first axial rotation plane 602 is in the vertical plane, and the first beam rotation surface 605 is a conical surface. The illustrative treatment beam (e.g., the center ray of the treatment beam) is tilted by an angle A with respect to the first axial rotation plane 602 during the rotation of the first gantry. In some embodiments, the angle A may be an acute angle, e.g., between 0° and 60°. For example, the angle A may be 30°, 40°, 50°, or 60°.

In some embodiments, the first radiation source 620 may tilt so that the angle of the treatment beam with respect to the rotation axis of the first gantry 630 (or the angle of the first beam (or treatment beam) with respect to the first axial rotation plane) may be adjusted. In order to adjust the orientation of the treatment beam, in some embodiments, the arm may be arranged to be extendable/retractable with respect to the first gantry; in some embodiments, the first radiation source 620 may be arranged to be movable, and/or tilt-able with respect to the arm; and in some embodiments, the arrangement may include a combination of the above-mentioned.

The second radiation source 641 may be configured to deliver an imaging beam (e.g., X-ray beam). In some embodiments, the imaging beam may cover an imaging region of the radiation system 100. In some embodiments, the second radiation source 641 may deliver the imaging beam when the first radiation source 620 delivers the treatment beam. That is, the treatment beam and the first imaging beam may be delivered simultaneously. In some embodiments, the delivery of the first imaging beam and the delivery of the treatment beam may alternate.

The radiation detector 642 may be configured to detect at least a portion of the imaging beam. In some embodiments, the radiation detector 642 may be a flat panel detector or a computed tomography detector. The shape of the radiation detector may be flat, arc-shaped, circular, or the like, or any combination thereof. Merely by way of example, the radiation detector may be a CT detector configured to detect X-ray beams. In some embodiments, the second radiation source 641 and the radiation detector 642 may form an imaging assembly having an imaging region of the radiation system 100. In some embodiments, the imaging assembly formed by the second radiation source 641 and the radiation detector 642 may have an isocenter. In some embodiments, the isocenter of the imaging assembly may coincide with the isocenter of the treatment beam generation assembly, i.e. the point 660. In some embodiments, the treatment beam may pass the isocenter 660 of the imaging assembly formed by the second radiation source and the first radiation detector.

In some embodiments, the second radiation source 641 may be mounted on an inner side of the second gantry 640. The second radiation source 641 may be moveable along the inner side of the second gantry 640. For example, the second radiation source 641 may be rotatably and/or translationaly moveable. In some embodiments, the second radiation source 641 may be rotatable about the isocenter of the second gantry 640. In some embodiments, the radiation detector 642 may be mounted on an inner side of the second gantry 640. The radiation detector 642 may be moveable along the inner side of the second gantry 640. For example, the radiation detector 642 may be rotatable and/or translational moveable. In some embodiments, the radiation detector 642 may be rotatable about the isocenter of the second gantry 640. In some embodiments, the imaging beam may include diagnostic X-rays, and the second radiation source 641 may include a diagnostic X-ray tube.

In some embodiments, the second radiation source 641 (or the radiation detector 642) may rotate about the rotation axis of the second gantry 640 or the isocenter 660 of the second gantry 640. The rotation of the second radiation source 641 (or the radiation detector 642) about the rotation axis of the second gantry 640 may define the second axial rotation plane. During the rotation of the second radiation source 641 (or the radiation detector 642), the center ray of the imaging beam may rotate about the rotation axis accordingly, defining a second beam rotation plane (or referred to as the imaging beam rotation plane). As illustrated in FIG. 6B, the second axial rotation plane and the second beam rotation plane may be in the same plane 604, the second axial rotation plane (and/or the second beam rotation plane) is in the vertical plane.

In some embodiments, the first radiation source 620 and the second radiation source 641 may be positioned such that the treatment region and the first imaging region may at least partially overlap. In some embodiments, the imaging beam may intersect with the first beam rotation surface 605. In some embodiments, the treatment beam may intersect with the second beam rotation plane 604. In some embodiments, the treatment region and the imaging region at least partially overlap. In some embodiments, the treatment beam is tilted with respect to the first axial rotation plane 602 such that the treatment beam passes an isocenter of the imaging assembly 406 formed by the second radiation source 641 and the radiation detector 642. In some embodiments, the treatment beam is tilted by an angle with respect to the first axial rotation plane 602. The angle may be an acute angle which ranges, e.g., between 0° and 60°. In the present embodiment as shown in FIGS. 6A and 6B, the treatment beam intersects with the second beam rotation plane 604 (imaging beam rotation plane) defined by the imaging beam. And/or, the imaging beam intersects with the first beam rotation surface 605 (treatment beam rotation surface) defined by the treatment beam. Moreover, the treatment beam (or the imaging beam) is not within the same plane with the imaging beam rotation plane 604 (or the treatment beam rotation surface). And/or the first beam rotation surface 605 and the second beam rotation plane 604 are in different planes.

It should be noted that the above description of the image-guided treatment apparatus 110 is merely provided for the purposes of illustration, and not intended to limit the scope of the present disclosure. For persons having ordinary skills in the art, multiple variations or modifications may be made under the teachings of the present disclosure. For example, the image-guided treatment apparatus 110 in FIG. 6A may further include one or more components, such as one or more connecting pieces to connect the first gantry 630 and the second gantry 640. As another example, the number of the radiation sources and/or the radiation detectors mounted on the first gantry 630 and/or the second gantry 640 is not limiting.

Figure 7A:
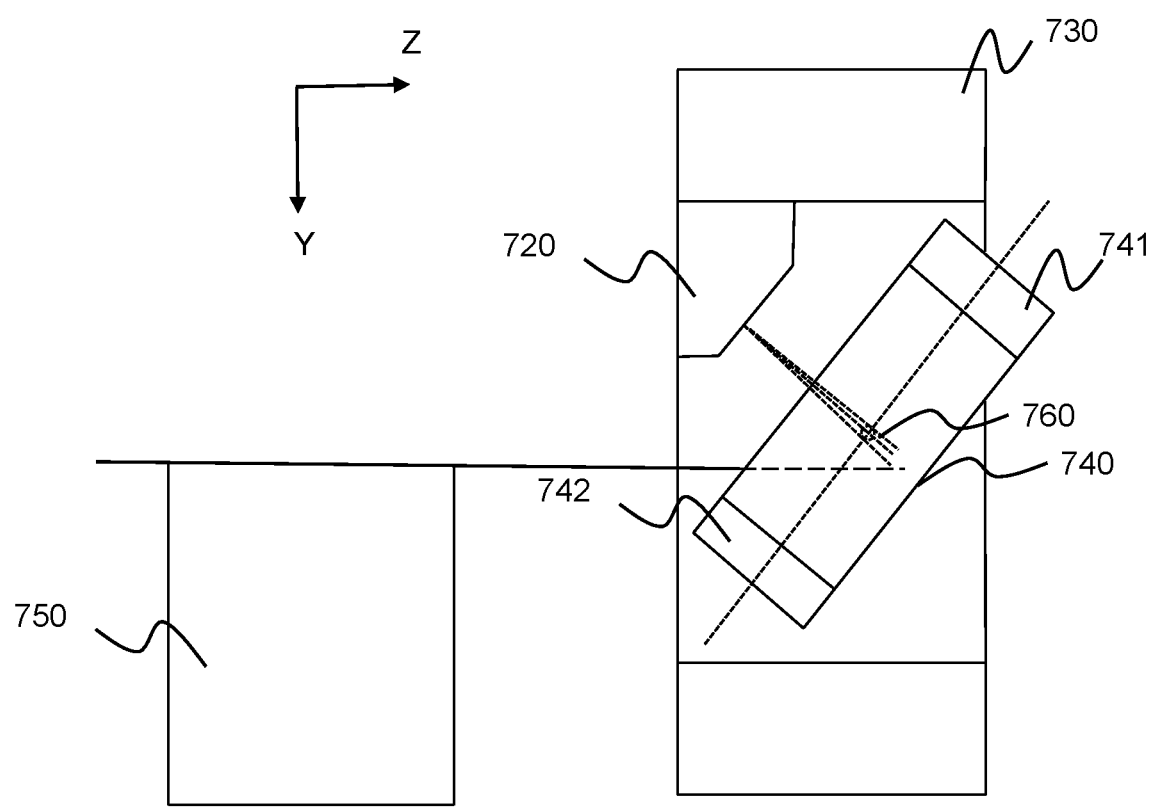
FIG. 7A is a schematic diagram illustrating the section view of an exemplary image-guided treatment device according to some embodiments of the present disclosure.
Figure 7B:
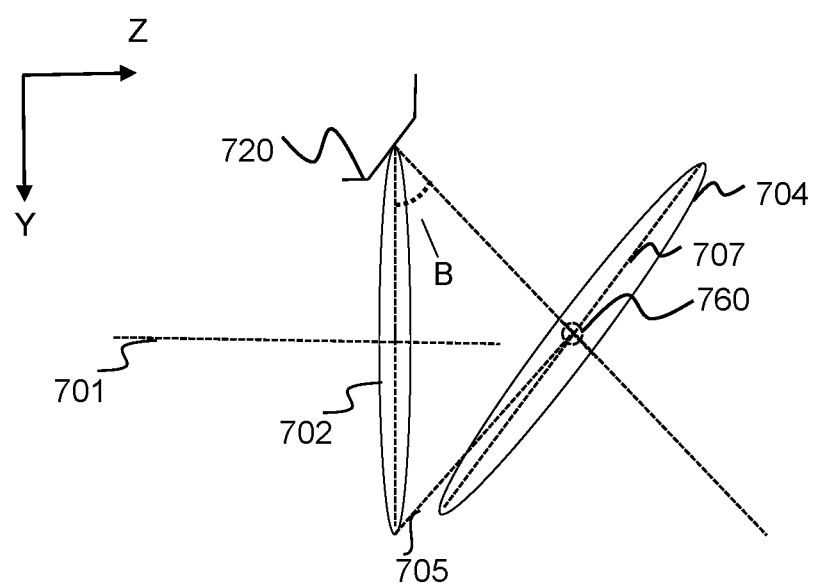
FIG. 7B is a schematic diagram illustrating rotation planes and beam rotation planes according to some embodiments of the present disclosure.

FIG. 7A a schematic diagram illustrating the section view in a Y-Z plane of an exemplary image-guided treatment apparatus 110 according to some embodiments of the present disclosure. FIG. 7B is a schematic diagram illustrating axial rotation planes and beam rotation planes according to some embodiments of the present disclosure.

As shown in FIG. 7A, the image-guided treatment apparatus 110 may include a first gantry 730, a second gantry 740, a first radiation source 720, a second radiation source 741, a detector 742 opposing the second radiation source 741, a table 750, and a base at least supporting the first gantry 730 (not shown). Both of the first gantry 730 and the second gantry 740 are ring-shaped. The second gantry 740 may be directly mounted on the base, or may be supported by the first gantry 730. The second gantry 740 may serve as a stator, and the second radiation source 741 and the radiation detector 742 may serve as a rotor mounted on said stator in rotation. In some embodiments, the second gantry 740 may serve as a rotor on which the second radiation source 741 and the radiation detector 742 may be fixedly connected. When the second gantry 740 may serve as the rotor, the coupling between the second gantry 740 and the base or the connection between the second gantry 740 and the first gantry 730 may be rotatable. The table 750 may be configured to support and/or transport the object (e.g., a patient) to be imaged and/or undergo radiotherapy.

The first gantry 730 may support the first radiation source 720. The second gantry 740 may support the second radiation source 741 and the detector 742. The rotation plane of the first gantry 730 and the rotation plane of the second gantry 740 may be non-parallel to each other. In some embodiments, the rotation plane of the second gantry 740 may be tilted by an acute angle with respect to the rotation plane of the first gantry 730. The acute angle may range between, for example, 0° and 45°.

The first radiation source 720 may be configured to deliver a treatment beam to an object (e.g., a patient) accommodated in a bore of the first gantry 730. The first gantry 730 may have a treatment region relating to the object. The second radiation source 741 and the radiation detector 742 may be respectively positioned at two different sides of the second gantry 740. The second gantry 740 may be directly mounted on the base in some embodiments, or may be supported by the first gantry 720 in the other embodiment. In some embodiments, the second gantry 740 may serve as a stator, and the second radiation source 741 and the radiation detector 742 may serve as a rotor rotatable with respect to said stator. In the other embodiment, the second gantry 740 may serve as a rotor on which the second radiation source 741 and the radiation detector 742 are equipped. The second radiation source 741 may deliver an imaging beam (e.g., X-ray beam) to the object in a substantially diagonal direction with respect to the vertical plane toward the radiation detector 742. The radiation detector 742 may be configured to detect at least a portion of the imaging beam. The second radiation source 741 and the radiation detector 742 may form an imaging assembly having an imaging region. The imaging assembly may have an isocenter. In some embodiments, the isocenter of the imaging assembly may coincide with the isocenter of the treatment beam generation assembly, that is, the point 760.

The first radiation source 720 and the second radiation source 741 may be rotatable. In some embodiments, the rotation of the first radiation source 720 may be independent of the second radiation source 741. In some embodiments, the first radiation source 720 and the second radiation source 741 may rotate synchronously, at same or different speeds. More description regarding the rotation of the first radiation source and the second radiation source may be found elsewhere in the present disclosure. See, e.g., FIG. 4 and the description thereof.

The first radiation source 720 may be rotatable about the rotation axis 701 of the first gantry 730. The rotation of the first radiation source 720 about the rotation axis 701 of the first gantry 730 may define a first axial rotation plane 702. As illustrated in FIG. 7B, the first axial rotation plane 702 is in the vertical plane. During the rotation of the first radiation source 720, the center ray of the treatment beam may rotate about the rotation axis 701 accordingly, defining a first beam rotation surface 705 (or referred to as a treatment beam rotation surface). The first beam rotation surface 705 is a conical surface. The illustrative treatment beam (e.g., the center ray of the treatment beam) may be tilted generally by an angle B with respect to the first axial rotation plane 702. In some embodiments, the angle B may be an acute angle, e.g., between 0° and 60°. For example, the angle B may be 30°, 40°, 50°, or 60°. During the rotation of the first radiation source 720, at least a portion of the treatment beam emitted by the first radiation source may pass the isocenter 760 of the second gantry 740. The second radiation source 741 (or the radiation detector 742) may be rotatable about the rotation axis 707 of the second gantry 740 and/or the isocenter 760 of the second gantry 740. The rotation of the second radiation source 741 (or the radiation detector 742) about the rotation axis 707 of the second gantry 740 may define a second axial rotation plane. The rotation of the center ray of the imaging beam about the isocenter 760 of the second gantry 740 may define a second beam rotation plane 704. FIG. 7B only illustrates a small portion of the second beam rotation plane 704. The second axial rotation plane and the second beam rotation plane may be in the same plane 704. As illustrated in FIG. 7B, the second axial rotation plane 704 (and/or the second beam rotation plane 704) may be at an oblique angle with the vertical plane. In some embodiments, the angle may be an acute angle, e.g., between 0° and 45°.

In some embodiments, as shown in FIG. 7A, the first radiation source 720 and the second radiation source 741 may be configured such that the treatment region and the first imaging region may at least partially overlap. In some embodiments, the imaging beam may intersect with the first beam rotation surface 705. In some embodiments, the treatment beam may intersect with the second beam rotation plane 704. In some embodiments, the treatment beam emitted by the first radiation source 720 may pass the imaging region of the imaging assembly formed by the second radiation source 741 and the radiation detector 742. In some embodiments, the treatment region and the imaging region at least partially overlap. In some embodiments, the treatment beam is tilted with respect to the first axial rotation plane 702 such that the treatment beam passes an isocenter 760 of the imaging assembly formed by the second radiation source 741 and the radiation detector 742. In some embodiments, the treatment beam is tilted by an angle with respect to the first axial rotation plane 702. The angle may be an acute angle which ranges, e.g., between 0° and 60°. In the present embodiment as shown in FIGS. 7A and 7B, the treatment beam intersects with the second beam rotation plane 704 (imaging beam plane) defined by the imaging beam. And/or, the imaging beam intersects with the first beam rotation surface 705 (treatment beam rotation surface) defined by the treatment beam. Moreover, the treatment beam (or the imaging beam) is not within the same plane with the imaging beam rotation plane 704 (or the treatment beam rotation surface). And/or the first beam rotation surface 705 and the second beam rotation plane 704 are the different planes.

Figure 8:
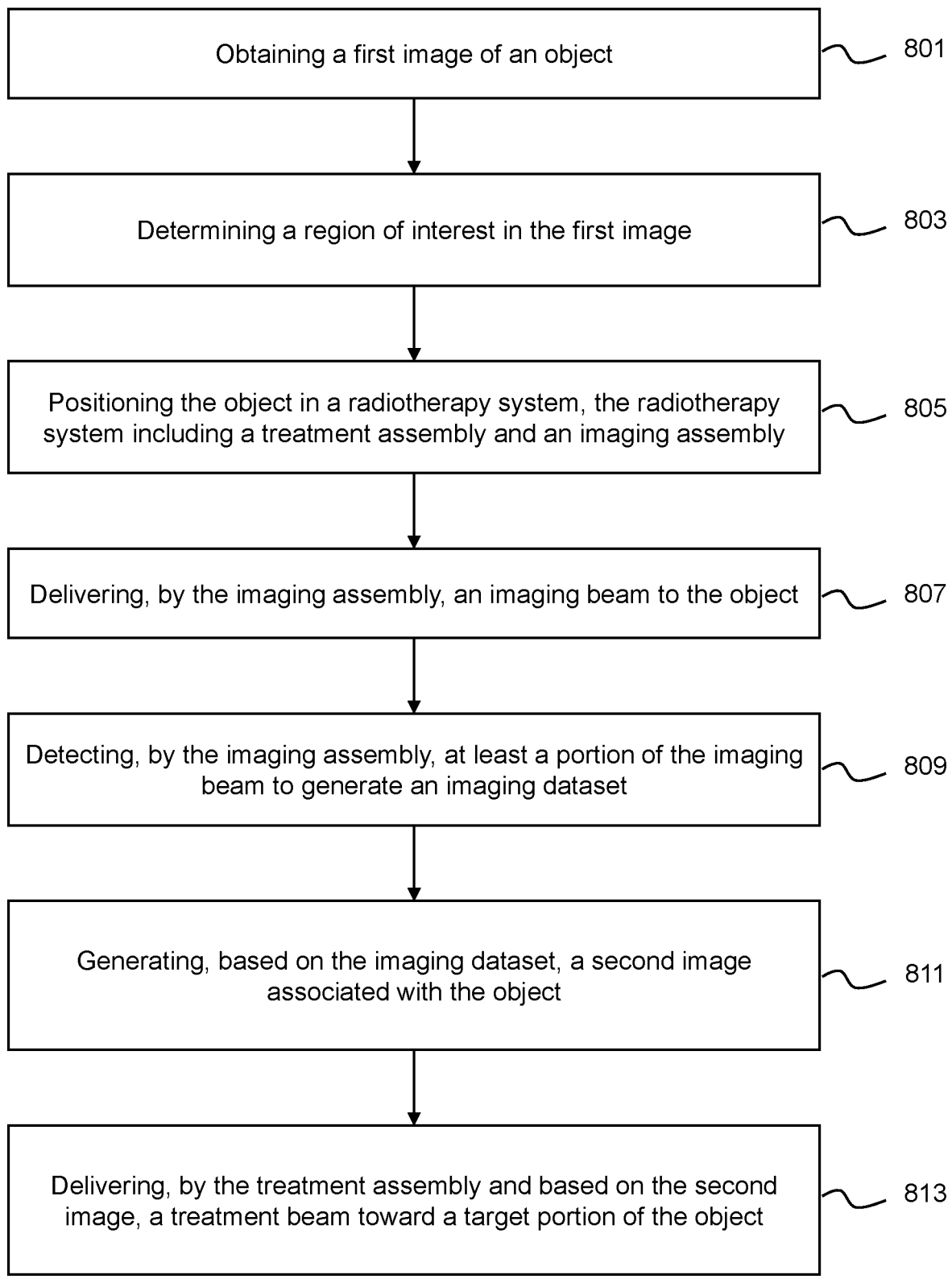
FIG. 8 is a flowchart illustrating an exemplary process/method for image-guided radiotherapy according to some embodiments of the present disclosure.

FIG. 8 is a flowchart illustrating an exemplary process 800 for image-guided radiotherapy according to some embodiments of the present disclosure. The process 800 may be executed by the radiation system 100. For example, the process 800 may be stored in the storage device 150 and/or the storage 220 as a form of instructions (e.g., an application), and invoked and/or executed by the processing device 150 (e.g., the processor 210 illustrated in FIG. 2, or one or more modules in the processing device 140 illustrated in FIG. 5). In some embodiments, one or more operations of the process 800 may be performed with manual intervention. The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 801, the processing device 140 (e.g., the acquisition module 502) may obtain a first image of an object. In some embodiments, the processing device 140 may obtain the first image from a storage device, for example, the storage device 150, or an external storage source (not shown). The first image may be generated using an imaging system. In some embodiments, the imaging system may be a computed tomography (CT) system. In some embodiments, the first image may be generated by an imaging assembly of the image-guided treatment apparatus 110. In some embodiments, the first image may be a two-dimensional (2D) image, a three-dimensional (3D) image, a four-dimensional (4D) image, etc. In some embodiments, the first image may be a planning image (e.g., a planning CT image) or a previously determined 3D or 4D image. The object may include a substance, a tissue, an organ, a specimen, a body, or the like, or any combination thereof. In some embodiments, the object may include a patient or a part thereof (e.g., a head, a breast, an abdomen, etc.). In some embodiments, the first image may be obtained based on one or more instructions or manipulations of an operator (e.g., a doctor). For example, the first image may be obtained based on one or more imaging parameters input or selected by the operator.

In 803, the processing device 140 (e.g., the processing module 506) may determine a region of interest (ROI) in the first image. The ROI may refer to a part of the object in the first image. In some embodiments, the ROI may be a region of cancerous and/or non-cancerous target which needs to be treated by the radiation system 100. The ROI may include a cell, a tissue, an organ (e.g., a prostate, a lung, a brain, a spine, a liver, a pancreas, a breast, etc.), or any combination thereof. In some embodiments, the ROI may be a tumor, an organ with tumor, or a tissue with tumor. In some embodiments, the processing device 140 may determine the ROI in the first image based on an image segmentation algorithm. The image segmentation algorithm may include a threshold algorithm, a region growing algorithm, an algorithm based on an energy function, a level set algorithm, a region segmentation and/or merging, an edge tracking segmentation algorithm, a statistical pattern recognition algorithm, a mean clustering segmentation algorithm, a model algorithm, a segmentation algorithm based on a deformable model, an artificial neural networks method, a minimum path segmentation algorithm, a tracking algorithm, a segmentation algorithm based on a rule, a coupling surface segmentation algorithm, or the like, or any combination thereof. In some embodiments, the ROI may be determined based on one or more instructions or manipulations of an operator (e.g., a doctor). For example, the ROI may be selected or edited by the operator.

In 805, the processing device 140 may position the object in a radiation system. The radiation system may include a treatment beam generation assembly and an imaging assembly (e.g., the radiation system 100 shown in FIG. 1). The first image may include information related to the location of the ROI. In some embodiments, the object may be positioned in a bore of the image-guided treatment apparatus 110 to receive radiation based on the information related to the location of the ROI. In some embodiments, the processing device 140 may determine a position relationship between the ROI in the first image and a treatment beam in the radiation system. In some embodiments, the processing device 140 (e.g., the control module 504) may position the object in the radiation system based on the position relationship, so that the object may be positioned in a treatment region of the radiation system. In some embodiments, the object may be positioned based on one or more instructions or manipulations of an operator (e.g., a doctor). For example, the position of the object may be adjusted by the operator before, during, and/or after the processing device 140 positions the object.

In some embodiments, the radiation system may include the image-guided treatment apparatus 110. The image-guided treatment apparatus 110 may include a treatment beam generation assembly and an imaging assembly. The treatment beam generation assembly may include a first radiation source in a first gantry. The imaging assembly may include a second radiation source and a radiation detector in a second gantry. The rotation plane of the first gantry and the rotation plane of the second gantry may be parallel or non-parallel to each other.

In 807, the imaging assembly (e.g., the second radiation source in the second gantry) may deliver an imaging beam (e.g., X-ray beam) to the object. In some embodiments, the imaging beam may be delivered based on one or more instructions or manipulations of an operator (e.g., a doctor). For example, the X-ray energy of the imaging beam may be set by the operator.

In 809, the imaging assembly (e.g., the radiation detector in the second gantry) may detect at least a portion of the imaging beam to generate an imaging dataset. In some embodiments, the imaging dataset may include raw data such as projection data. In some embodiments, the second radiation source in the second gantry may deliver the imaging beam toward the radiation detector in a substantially diagonal direction. The radiation detector may detect at least a portion of the imaging beam to generate the imaging dataset.

In 811, the processing device 140 (e.g., the processing module 506) may generate, based on the imaging dataset, a second image associated with the object (e.g., the ROI, or a reference portion of the object). The reference portion may be a surrogate region (e.g., a diaphragm), so that a target portion (e.g., a lung, a liver, a stomach, etc.) to be treated by radiation may be addressed and located in the treatment region of the radiation system 100. In some embodiments, the processing device 140 may reconstruct the second image based on the imaging dataset according to a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the second image may include the ROI. In some embodiments, the second image may include a surrogate region (e.g., a diaphragm) instead of the ROI. In some embodiments, the second image may be generated based on one or more instructions or manipulations of an operator (e.g., a doctor). For example, one or more reconstruction parameters may be set by the operator.

In some embodiments, the processing device 140 may reconstruct an image based on the imaging dataset(s) acquired by imaging assemblies as illustrated in FIGS. 7 and 8, in combination with additional imaging dataset by another imaging assembly of the image-guided treatment apparatus 110, or by another CT device. For instance, such additional imaging dataset may be acquired by a further imaging assembly of the image-guided treatment apparatus 110. The further imaging assembly may be formed by a radiation source and a radiation detector located in the same gantry (e.g, the second gantry) in which the imaging beam passes through the isocenter thereof.

In some embodiments, the processing device 140 may augment or supplement at least a portion of the imaging dataset based on data derived from one or more reference images including, for example, a planning CT and/or a previously determined 3D or 4D image (e.g., the first image). Merely by way of example, the processing device 140 may analyze or determine what data are missing based on a trajectory of the imaging assembly; the processing device 140 may determine corresponding data in the reference image(s) that can be used to augment the missing data; and the processing device 140 may insert the corresponding data to supplement the missing data. In some embodiments, in the data augmentation operation, the processing device 140 may use one or more tomographic consistency conditions derived from the first image, so that the image quality of the second image may be improved.

In 813, the treatment beam generation assembly (e.g., the first radiation source) may deliver, based on the second image, a treatment beam toward a target portion of the object. The target portion of the object may correspond to the ROI in the second image. The treatment beam and the imaging beam are in different planes. The second image may include information related to the ROI or the reference portion, such as the location of the ROI, the location of the reference portion. The treatment beam generation assembly may deliver the treatment beam toward the target portion of the object that conforms to the location of the ROI. In some embodiments, the processing device 140 may detect a movement or change of the target portion of the object based on the second image. The processing device 140 may revise the delivery of the treatment beam or the position of the object. For example, the processing device 140 may pause the delivery of the treatment beam, and then adjust the radiation source (e.g., the first radiation source) of the treatment beam generation assembly to target at the location of the moved or changed target portion of the object. As another example, the processing device 140 may pause the delivery of the treatment beam, and then adjust the position of the target portion of the object with respect to the treatment beam to make the treatment beam target at the target portion. The processing device 140 (e.g., the control module 504) may adjust the position of the object by moving the object in a table (e.g., the table 114) in the bore of the treatment beam generation assembly. After the delivery of the treatment beam or the position of the object is adjusted, the treatment beam generation assembly may resume the delivery of the treatment beam. In some embodiments, when detecting the movement or change of the target portion, the treatment beam generation assembly may terminate the delivery. In some embodiments, the processing device 140 may generate a notification based on the detected movement or change of the target portion of the object. In some embodiments, the notification may include information of the movement or change of the target portion. The notification may be in a form of text, video, audio, etc.

In some embodiments, the delivery of the treatment beam in 813 and the delivery of the imaging beam in 807 may be performed simultaneously. In some embodiments, the delivery of the treatment beam in 813 and the delivery of the first imaging beam in 807 may be performed alternately. Therefore, the imaging assembly may track the motion of the target portion of the object while the treatment beam is delivered or from time to time.

In some embodiments, the generation of the second image in 811 may be unnecessary, and accordingly, the treatment beam may be delivered based on at least a portion of the imaging dataset (or processed imaging dataset) instead of the second image. Merely by way of example, in 913, the processing device 140 may analyze projection data corresponding to at least a portion of the imaging dataset or processed imaging dataset (e.g., compare the projection data with reference projection data) to infer the position/trajectory of the ROI (or the target portion of the object), and deliver the treatment beam based on the position/trajectory of the ROI.

It should be noted that the above description of the process 800 for radiotherapy is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. For example, an operation for adjusting the position of the target portion of the object and/or revising the treatment beam may be added between operations 811 and 813.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation system, comprising:
   a treatment assembly including a first radiation source configured to deliver a treatment beam, the treatment assembly having a treatment region relating to an object;
   a first gantry supporting the first radiation source, wherein the first radiation source is located within a bore defined by the first gantry and mounted on an inner side of the first gantry;
   an imaging assembly including a second radiation source and a radiation detector, the second radiation source being configured to deliver an imaging beam, and the radiation detector being configured to detect at least a portion of the imaging beam, the imaging assembly having an imaging region relating to the object; and
   a second gantry supporting the second radiation source and the radiation detector, wherein the second gantry is located within the first gantry;

wherein the first radiation source is rotatable in a first plane, the second radiation source is rotatable in a second plane different from the first plane, such that the treatment region and the imaging region at least partially overlap.

2. The radiation system of claim 1, wherein the treatment beam passes through an isocenter of the imaging assembly.

3. The radiation system of claim 2, wherein the treatment beam and the imaging beam intersect at the isocenter of the imaging assembly.

4. The radiation system of claim 1, wherein the first radiation source is located outside of a bore defined by the first gantry.

5. The radiation system of claim 4, further including an arm mounted on the first gantry, the first radiation source being mounted on the arm.

6. The radiation system of claim 1, wherein a rotation plane of the first gantry and a rotation plane of the second gantry are parallel during a radiotherapy operation.

7. The radiation system of claim 1, wherein a rotation plane of the second gantry is tilted with respect to a rotation plane of the first gantry.

8. The radiation system of claim 1, wherein the first gantry and the second gantry are rotatable synchronously.

9. The radiation system of claim 1, wherein the first gantry is configured to rotate independently of the second gantry.

10. The radiation system of claim 1, further comprising:
a processing module configured to reconstruct an image based on the at least portion of the imaging beam detected by the radiation detector when the first radiation source delivers the treatment beam.

11. The radiation system of claim 10, wherein the processing module, based on the reconstructed image, causes the first radiation source to deliver an adjusted treatment beam.

12. The radiation system of claim 10, wherein the processing module, based on the reconstructed image, causes a position of the object to be adjusted with respect to the treatment beam.

13. The radiation system of claim 1, wherein the delivery of the treatment beam and the delivery of the imaging beam are simultaneous or alternate.

14. The radiation system of claim 1, wherein the radiation detector is a flat panel detector or a computed tomography detector.

15. The radiation system of claim 1, wherein the second plane is parallel to the first plane.

16. The radiation system of claim 1, wherein the second plane is tiled by an angle with respect to the first plane, the angle being an acute angle ranging between 0° and 45°.

17. The radiation system of claim 1, wherein a rotation speed of the first gantry is lower than a rotation speed of the second gantry.

18. A radiation system, comprising:
a treatment assembly including a first radiation source configured to deliver a treatment beam, wherein the treatment beam forms a treatment beam rotation surface during rotation of the first radiation source;
a first gantry supporting the first radiation source, wherein the first radiation source is located within a bore defined by the first gantry and mounted on an inner side of the first gantry;
an imaging assembly including a second radiation source and a radiation detector, the second radiation source being configured to deliver an imaging beam, and the radiation detector being configured to detect at least a portion of the imaging beam, wherein the imaging beam forms an imaging beam rotation plane during rotation of the imaging assembly; and
a second gantry supporting the second radiation source and the radiation detector wherein the second gantry is located within the first gantry;
wherein the imaging beam rotation plane intersects with the treatment beam rotation surface such that a portion of a subject is irradiated by the imaging beam and the treatment beam.

19. A radiation system, comprising:
a treatment assembly including a first radiation source configured to deliver a treatment beam;
a first gantry supporting the first radiation source, wherein the first radiation source is located within a bore defined by the first gantry and mounted on an inner side of the first gantry;
an imaging assembly including a second radiation source and a radiation detector, the second radiation source being configured to deliver an imaging beam, and the radiation detector being configured to detect at least a portion of the imaging beam; and
a second gantry supporting the second radiation source and the radiation detector, wherein the second gantry is located within the first gantry;
wherein the first radiation source is configured to rotate about a rotation axis of the first gantry, defining a plane; and
the treatment beam delivered by the first radiation source is tilted with respect to the plane such that the treatment beam passes an imaging region of the imaging assembly.

* * * * *